United States Patent [19]

Honna et al.

[11] 4,022,845

[45] May 10, 1977

[54] PROCESS FOR PRODUCING ALKYL ADAMANTANES

[75] Inventors: Kosaku Honna, Chiba; Nobuaki Shimizu, Fukuoka; Konomu Kurisaki, Chiba, all of Japan

[73] Assignee: Idemitsu, Kosan Kabushiki-Kaisha (Idemitsu Kosan Co., Ltd.), Tokyo, Japan

[22] Filed: May 28, 1976

[21] Appl. No.: 690,862

[52] U.S. Cl. .................. 260/666 M; 260/666 PY; 208/DIG. 1
[51] Int. Cl.$^2$ ........................................... C07C 5/24
[58] Field of Search .............. 260/666 M, 666 PY; 208/DIG. 1

[56] References Cited

UNITED STATES PATENTS

| | | | |
|---|---|---|---|
| 3,637,876 | 1/1972 | Bagry | 260/666 M |
| 3,944,626 | 3/1976 | Honna et al. | 260/666 M |

FOREIGN PATENTS OR APPLICATIONS 2,419,620  11/1974  Germany ............... 260/666 M

OTHER PUBLICATIONS

Raymond C. Fort et al., Chem. Rev. vol. 64, No. 3, pp. 277–300, 1964.
Chem. Ab. 57:4938a.

Primary Examiner—Veronica O'Keefe
Attorney, Agent, or Firm—Flynn & Frishauf

[57] ABSTRACT

This invention relates to a process for producing alkyl adamantanes by reacting tetracyclododecanes and hydrogen in the presence of a specific catalyst.

8 Claims, No Drawings

PROCESS FOR PRODUCING ALKYL ADAMANTANES

BACKGROUND OF THE INVENTION a. Field of the invention

The present invention relates to a process for producing alkyl adamantanes.

According to the present invention, alkyl adamantanes can be produced efficiently from tetracyclododecanes which is prepared by using such petrochemical materials as dicyclopentadiene.

b. Description of the prior art

Heretofore, upon producing tricyclic adamantane skeleton, method comprising hydrogenation of such tricyclic compounds as acenaphthene, fluorene, anthracene, phenanthrene etc. and then isomerization of them have been widely used. For example, in order to obtain 1,3-dimethyl adamantane perhydroacenaphthene which is prepared by complete hydrogenation of acenaphthene has been employed. However, in this method, costs become high, for the starting material, acenaphthene, is prepared by distillation of coal tar and thus its supply is very limited in quantity. Moreover, complete hydrogenation of acenaphthene required very drastic condition which causes many difficulties in actual operation.

Recently, a method of producing alkyl adamantane ($C_{12}H_{20}$) by using tetracyclic compound as starting material in the presence of $AlBr_3$ or a sludge of $AlBr_3$ has been reported, but its reaction yield is very low and this method is not satisfactory for practical application.

SUMMARY OF THE INVENTION

This invention relates to a process for producing alkyl adamantanes.

In the process of this invention, the reaction of tetracyclododecanes and hydrogen is carried out in the presence of H-Y type zeolite or zeolite.

DESCRIPTION OF THE PREFERRED EMBODIMENTS

The present invention relates to a process for producing alkyl adamantanes. More particularly, this invention relates to a process for producing alkyl adamantanes efficiently by reacting tetracyclododecanes and hydrogen in the presence of a specific catalyst.

Dicyclopentadiene which is present abundantly in petroleum distillates can be utilized as a starting material for preparing tetracyclododecanes. Thus, practical process for the production of alkyl adamantanes can be provided if tetracyclododecanes are utilized for the starting material of the process.

We found the tetracyclododecanes can be converted into alkyl adamantanes with a good yield by hydrogenation and isomerization in the presence of the specific catalyst.

As to tetracyclododecanes, tetracyclo-$(6.2.1.1^{3,6}.0^{2,7})$ dodecane and its lower (ex. $C_1 - C_4$) alkyl derivatives (designates as "tetracyclo-$(6.2.1.1^{3,6}.0^{2,7})$ dodecanes" hereafter) can be used as a starting material of the process of this invention.

Tetracyclo-$(6.2.1.1^{3,6}.0^{2,7})$ dodecanes can be obtained from dicyclopentadiene as shown in the following. That is, dicyclopentadiene and olefin are reacted by Diels-Alder reaction under heating to form tetracyclododecene and its derivatives. An example of this reaction can be shown by a chart below, where (A) indicates dicyclopentadiene.

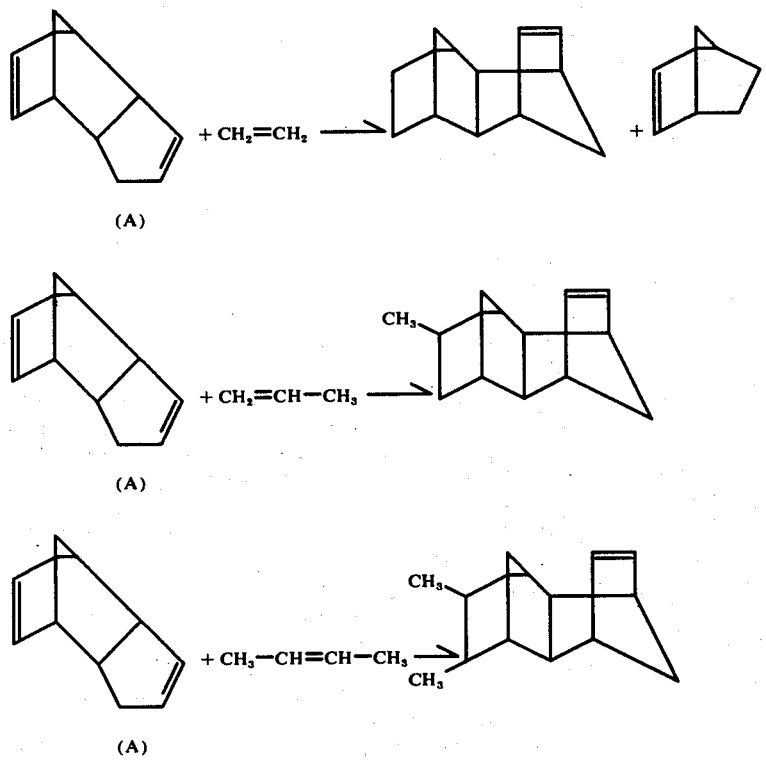

(A)

(A)

(A)

And the, tetracyclododecene and their derivatives thus obtained are hydrogenated to form the starting material of the present invention; tetracyclo-$(6.2.1.1^{3,6}.0^{2,7})$ dodecanes. An example of this hydrogenation can be shown as below, where (B) indicates tetracyclo-(6.2.1.1$^{3,6}$.0$^{2,7}$) dodecane.

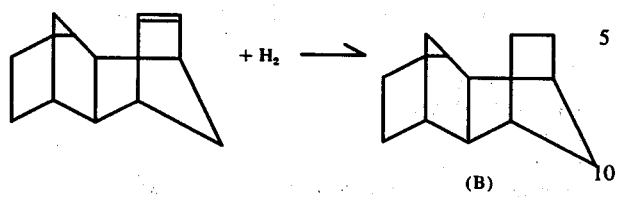

(B)

In the present invention, tetracyclo-(6.2.1.1$^{3,6}$.0$^{2,7}$) dodecanes obtained as above are reacted with hydrogen in the presence of the specific catalyst, and hydrogenation and rearrangement of carbon-carbon bonds are made to produce alkyl adamantanes.

A typical example of the process of the present invention can be shown by the following reaction sequence.

earth metals or rare earth metals are employed preferably.

As to preferable catalysts used in the present invention, in addition to the above-described examples, H-Y type zeolite or ion-exchanged zeolite which is further contained one or more than two of transitional metals selected from the group consisting of iron, cobalt, nickel, platinum, rhenium, copper, germanium, ruthenium, rhodium, osmium, iridium, molybdenum,, tungsten, silver etc. In this case, those containing platinum, rhenium or iron group metals such as iron, nickel and cobalt are especially preferable. For example, total contents of platinum and rhenium are set at 0.1 ~ 5% based on the weight of catalyst and the atomic ratio of platinum to rhenium is set at 19:1 ~ 1:3. In general, platinum or platinum compound is preferably set at below 1%. On the other hand, in the case of iron group metals, it is preferable to set at 0.1 ~ 10% based on the weight of catalyst. Germanium is set at below 0.1% in

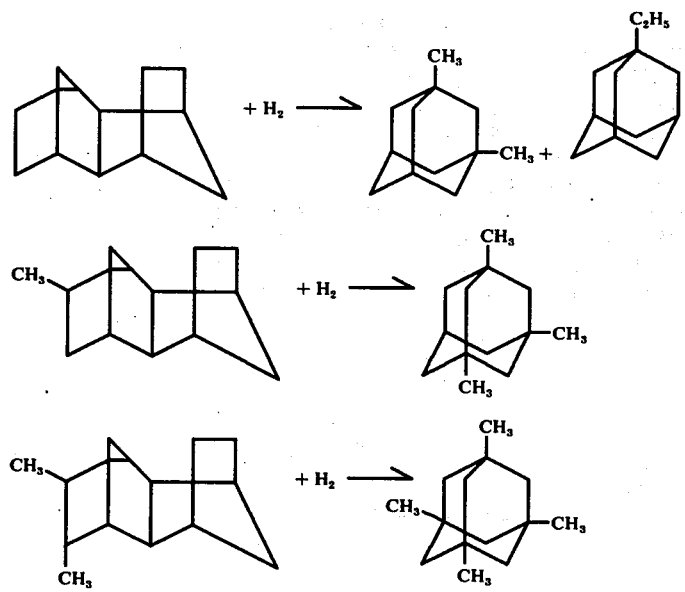

As described above, catalyst used in the present invention is (1) H-Y type zeolite or (2) zeolite which is subjected to ion-exchange with one or more than two metal ions selected from the group consisting of alkaline earth metals and rare earth metals (designated as "ion-exchanged zeolite" hereafter) or (3) mixture of (1) and (2). H-Y type zeolite is not necessarily a specific type, but commercially available products can be used for this purpose and it also can be prepared from NH$_4$-Y type zeolite by calcining. On the other hand, the above ion-exchanged zeolite is a product of X-, Y-type zeolites etc. of which cationic site such as Na$^+$, K$^+$ and NH$_4^+$ has been subjected to ion-exchange with alkaline earth metal such as Ca, Mg etc. or rare earth metal such as La, Ce, Nd, Yb, Y etc. This catalyst can be prepared by introducing ions of these metals of alkaline earth metals or rare earth metals in the form of aqueous solution of metal salt and followed by drying and calcining it. In this case, it is needed that the above metals are not carried by zeolite but they must be ion-exchanged with cationic site of the zeolite. Furthermore, in the present invention zeolite of which 30 ~ 100%, preferably 50 ~ 90% of cationic site such as Na$^+$, K$^+$, NH$_4^+$ etc. has been ion-exchanged by alkaline order to prevent the deterioration of the catalyst. These transitional metals have dehydrogen-hydrogenation ability.

Moreover, upon inclusion of metals to zeolite, not only ion-exchange method but also impregnation method etc. can also be employed. That is, the processes described in the specifications of Japanese Patent Application; 84869/1973, 21986/1974 and 56154/1974.

Activation of catalysts can be made by heating at 350 ~ 570° C in the stream of inert gas. Shape of catalysts can be made into any desired form such as powder or particles.

On practicing the present invention by a batch-wise system, it is preferable to feed the starting material, tetracyclo-(6.2.1.1$^{3,6}$.0$^{2,7}$) dodecanes, into a sealed vessel such as autoclave at a ratio of 0.5 ~ 5 to 1 of the above-mentioned catalyst by weight. When the ratio is below 0.5, it is very difficult to agitate and it tends to cause hydrogenation decomposition. On the other hand, when the ratio is larger than 5, it is difficult to proceed the reaction and to isomerize alkyl adamantanes formed to 1,3-dimethyl adamantane.

The reaction should be carried out under the conditions of reaction pressure of 5 ~ 50 kg/cm$^2$ by introducing $H_2$ gas, reaction temperature of 200°–350° C, and reaction time of 0.5 ~ 7 hours. When the pressure is higher than 50 kg/cm², hydrogenation decomposition tends to occur. When the pressure is less than 5 kg/cm², hydrogenation is difficult to occur and moreover inactivation of catalyst may occur before isomerization to adamantane skeleton. When reaction temperature is below 200° C, the reaction is difficult to proceed and especially isomerization to 1,3-dimethyl adamantane is difficult to occur. When temperature is above 350° C, it is not preferable due to stimulation of hydrogenation decomposition. When the reaction time is longer than 7 hours, decomposition of the product occurs and the yield is to decrease. When the reaction time is shorter than 0.5 hours, it is not preferable due to incomplete isomerization of product to 1,3-dimethyl adamantane. Furthermore, it is preferable to introduce hydrogen chloride gas together with hydrogen gas in the reaction vessel, in order to improve selectivity of the reaction. In this case, the amounts of hydrogen chloride gas is preferable to set at 2 – 20 mole % based on the amount of hydrogen gas.

The process of the present invention can be carried out not only by batch-wise system but also by continuous system.

According to the process of the present invention, inexpensive petrochemical materials such as dicyclopentadiene can be used for the production of alkyl adamantane efficiently, and industrially profitable process can be achieved.

Alkyl adamantanes thus obtained can be used for the production of synthetic lubricants, additives for lubricants, starting materials for monomer, medicines and for intermediates for organic synthesis.

The present invention is described in detail by the following examples.

EXAMPLE 1

1. Preparation of the catalyst $NH_4$-Y type zeolite (SK-41, Union Carbide Co. Ltd.) comprising $(NH_4)_2O$ 9.6 weight %, $Na_2O$ 2.4 weight %, $SiO_2$ 65 weight % and $Al_2O_3$ 23 weight % was calcined for 10 minutes at 250° C in the stream of air and then reduced for 1.5 hours at 400° C in the stream of hydrogen gas.

2. Reaction

Into a 100 ml content autoclave, 2.0 grams of zeolite prepared as above and 2.0 grams of tetracyclo-(6.2.1.1$^{3,6}$.0$^{2,7}$) dodecane were placed quickly and after evacuation hydrogen chloride gas was introduced to 1.5 kg/cm² followed by hydrogen gas to total pressure of 30 kg/cm². The reaction was carried out for 4 hours at 250° C with stirring. After the reaction, n-tridecane was added to the reaction mixture and then the catalyst (zeolite) and the reaction solution was separated by filtration. The reaction solution was analysed using p-cymene as the internal standard by gas chromatography. As the result, conversion yield of tetracyclo-(6.2.1.1$^{3,6}$.0$^{2,7}$) dodecane, selectivity of 1,3-dimethyl adamantane, yield of 1,3-dimethyl adamantane, selectivity of 1-ethyl adamantane, and yield of 1-ethyl adamantane were 21.5%, 9.3%, 2.0%, 15.2% and 3.3%, respectively.

EXAMPLE 2

1. Preparation of the catalyst

Ten grams of $NH_4$-Y type zeolite (SK-41, Union Carbide Co. Ltd.) were added to each of 1 liter of aqueous solution of 0.02 N $Ca(NO_3)_2.4H_2O$, $Mg(NO_3)_2.6H_2O$, $La(NO_3)_3.6H_2O$ or $Ce(NO_3)_3.6H_2O$ and subjected to ion-exchange at 80° C for 10 hours with stirring. Subsequently, these solutions were filtered at room temperature and cakes thus obtained were washed with 1 liter of pure water. After repreating the above procedure twice, they were dried at 250° C for 10 minutes in the stream of air and finally reduced at 400° C for 1.5 hours in the stream of hydrogen gas.

2. Reaction

The reaction was carried out in the same manner as described in Example 1 (2) except that the above described ion-exchanged zeolite was used as the catalyst. The results are shown in Table 1.

Table 1

| Catalyst | | Conversion of starting material (%) | 1,3-Dimethyl adamantane | | 1-Ethyl adamantane | |
| --- | --- | --- | --- | --- | --- | --- |
| Metal for ion-exchanging | Rate of ion-exchange (%) | | Selctivity (%) | Yield (%) | Selectivity (%) | Yield (%) |
| Ca | 70 | 25.1 | 12.6 | 3.2 | 16.3 | 4.1 |
| Mg | 70 | 20.3 | 7.0 | 1.4 | 9.8 | 2.0 |
| La | 55 | 32.9 | 10.0 | 3.3 | 15.8 | 5.2 |
| Ce | 55 | 32.4 | 9.1 | 2.9 | 14.4 | 4.7 |

EXAMPLE 3

1. Preparation of the catalyst

To 100 g of $NH_4$-Y type of zeolite (SK-41, Union Carbide Co. Ltd.), 300 ml of aqueous solution containing 7.74 grams of $Ni(NO_3)_2.6H_2O$ or $Co(NO_3)_2.6H_2O$ were poured and mixed throughly. After evaporation, colcinning and reduction were performed as described in Example 1 (1).

2. Reaction

The reaction was carried out in the same manner as described in Example 1 (2) except that the above-described zeolite was used as the catalyst. The results are shown in Table 2.

Table 2

| Kind and Amount of Metal being carried on catalyst | Conversion of starting material (%) | 1,3-Dimethyl adamantane | | 1-Ethyl adamantane | |
| --- | --- | --- | --- | --- | --- |
| | | Selectivity (%) | Yield (%) | Selectivity (%) | Yield (%) |
| Ni (3 wt %) | 22.3 | 8.3 | 1.9 | 11.9 | 2.7 |
| Co (3 wt %) | 24.5 | 12.1 | 3.0 | 18.3 | 4.5 |

EXAMPLE 4

1. Preparation of the catalyst

To 100 g of Y-type zeolite that was ion-exchanged as described in Example 2 (1), 300 ml of aqueous solution containing 77.4 grams of $Ni(NO_3)_2 \cdot 6H_2O$ or $Co(NO_3)_2 \cdot 6H_2O$ were poured and mixed thoroughly, and then 2076 cc of aqueous solution of Pt ($H_2PtCl_6$, 1.930 × $10^{-3}$ mol/l), 374 cc of aqueous solution of Re ($NH_4ReO_4$, 3.727 × $10^{-3}$ mol/l), and 1.85 cc of aqueous solution of Ge ($GeCl_4$, 1 g/100 cc of $CCl_4$) were added, if required. After evaporation, calcinning and reduction were performed in the same manner as described in Example 1 (1). (2) Reaction The reaction was carried out in the same manner as described in Example 1 (2) except that the above-described zeolite was used as the catalyst. The results are shown in Table 3.

scribed pressure, and then the reaction was carried out under the prescribed condition of temperature and time. After the completion of the reaction, products were analyzed by the same method as described in Example 1 (2). The results are shown in Table 4.

Table 4

| Type of Zeolite | Catalyst | | Starting material Catalyst | Pressure(kg/cm²) | | Temperature (°C) | Time (hr) | Conversion of starting material(%) | 1,3-Dimethyl adamantane | | 1-Ethyl adamantane | |
|---|---|---|---|---|---|---|---|---|---|---|---|---|
| | Metal for ion-exchanging and Rate of ion-exchange (%) | Kind and Amount of Metal being carried on catalyst (weight %) | | Total Pressure | Partial Pressure of HCl | | | | Selectivity (%) | Yield (%) | Selectivity (%) | Yield (%) |
| Na-Y | La(55), Ca(40) | Ni(3),Pt(0.75), Re(0.25) | 2 | 15 | 1 | 250 | 2 | 49.1 | 2.4 | 1.2 | 7.5 | 3.7 |
| " | " | " | 1 | 15 | 1 | 250 | 2 | 70.1 | 4.0 | 2.8 | 11.3 | 7.9 |
| " | " | " | 1 | 15 | 1 | 250 | 4 | 100 | 15.8 | 15.8 | 21.9 | 21.9 |
| " | " | " | 1 | 15 | 1 | 250 | 6 | 100 | 27.1 | 27.1 | 33.4 | 33.4 |
| NH₄-Y | La(55) | " | 1 | 15 | 1 | 250 | 4 | 100 | 14.9 | 14.9 | 20.3 | 20.3 |
| " | " | " | 1 | 15 | 1 | 300 | 4 | 100 | 28.0 | 28.0 | 0.6 | 0.6 |
| " | " | " | 2 | 15 | 1 | 300 | 4 | 100 | 41.9 | 41.9 | 19.3 | 19.3 |
| " | " | " | 1 | 40 | 1 | 250 | 4 | 100 | 47.7 | 47.7 | 18.2 | 18.2 |

COMPARATIVE EXAMPLE 1

The reaction was carried out in the same manner as described in Example 1 (2) except that as the catalyst, silica-alumina catalyst for FCC ($SiO_2$: $Al_2O_3$ = 87:13 by weight) carrying Ni, Pt and Re was used.

It was confirmed that the starting materials did not react at all.

COMPARATIVE EXAMPLE 2

Table 3

| No. | Catalyst | | Conversion of starting material (%) | 1,3-Dimethyl adamantane | | 1-Ethyl adamantane | |
|---|---|---|---|---|---|---|---|
| | Metal for ion-exchanging and Rate of ion-exchange (%) | Kind and Amount of Metal being carried on catalyst (weight %) | | Selectivity (%) | Yield (%) | Selectivity (%) | Yield (%) |
| 1 | La(55) | Ni(3) | 29.6 | 12.2 | 3.7 | 17.1 | 5.1 |
| 2 | La(55) | Co(3) | 35.7 | 14.3 | 5.1 | 19.6 | 7.0 |
| 3 | — | Ni(3),Pt(0.75) Re(0.25) | 92.0 | 25.6 | 23.5 | 20.3 | 18.7 |
| 4 | Ca(70) | " | 100 | 25.0 | 25.0 | 4.2 | 4.2 |
| 5 | Mg(70) | " | 75.0 | 5.7 | 4.3 | 12.7 | 9.5 |
| 6 | La(55) | " | 100 | 49.3 | 49.3 | 15.4 | 15.4 |
| 7 | Ce(55) | " | 100 | 29.4 | 29.4 | 5.1 | 5.1 |
| 8 | La(55) | " | 100 | 54.5 | 54.5 | 12.5 | 12.5 |
| 9 | La(55) | Ni(3),Pt(0.75) Re(0.25), Ge(0.001) | 100 | 52.7 | 52.7 | 10.0 | 10.0 |
| 10*¹ | La(55) | Ni(3),Pt(0.75) Re(0.25) | 100 | 10.8 | 10.8 | Others are hydrogenation decomposition products | |
| 11*² | — | " | 78.4 | 14.3 | 11.2 | 26.7 | 20.9 |

*¹:Hydrogen chloride gas was not introduced.
*²:Reaction time; 2 hours.

EXAMPLE 5

1. Preparation of the catalyst

The same treatment as shown in Example 4 (1) was done on NH₄-Y type zeolite (SK-41, Union Carbide Co. Ltd.) or Na-Y type zeolite (SK-40, Union Carbide Co. Ltd.) consisting of $Na_2O$ 13.0 weight %, $SiO_2$ 63.5 weight % and $Al_2O_3$ 23.5 weight %.

2. Reaction

Into 100 ml content autoclave, 2.0 grams of the catalyst and prescribed amounts of tetracyclo-(6.2.1.1³,⁶.0²,⁷) dodecane were placed quickly and after evacuation, introduction of hydrogen chloride gas followed by hydrogen gas was introduced up to the pre- By adding $AlBr_3$ slowly to $CS_2$ solution of ethyl bromide with cooling to 0° C, sludge catalyst of $AlBr_3$ was prepared and it was warmed to room temperature (20° C), and then two times amounts(based on the amount of the catalyst) of the starting material, tetracyclo-(6.2.1.1³,⁶.0²,⁷) dodecane were added gradually followed by stirring for 20 hours. Reaction products were analyzed in the same manner as in Example 1 (2) and it was found that conversion yield was 15%, but 1-ethyl adamantane and 1,3-dimethyl adamantane were not detected at all.

EXAMPLE 6 – 13 matography using p-cymene as the internal standard. The results at a steady state are shown in Table 5.

Table 5

| Ex. | Temp. (°C) | Pressure (kg/cm²) | Conc. of HCl (%) | LHSV (hr⁻¹) | Conversion rate (%) | Selectivity[1] of $C_{12}$Ad.(%) | Selectivity[2] of DMA (%) |
|---|---|---|---|---|---|---|---|
| 6  | 220 | 30 | 5.36 | 0.21 | 57   | 62.5 | 39   |
| 7  | 240 | 30 | 5.36 | 0.21 | 62   | 37.5 | 26   |
| 8  | 220 | 20 | 5.36 | 0.21 | 44   | 57   | 34   |
| 9  | 200 | 30 | 5.36 | 0.21 | 45   | 73   | 36   |
| 10 | 220 | 30 | 2.2  | 0.21 | 76   | 60   | 32   |
| 11 | 200 | 30 | 2.2  | 0.21 | 47.5 | 64   | 29   |
| 12 | 220 | 30 | 2.2  | 0.44 | 46   | 62.5 | 36   |
| 13 | 200 | 35 | 2.2  | 0.20 | 62   | 55   | 32.5 |

[1] $C_{12}$Ad represents $C_{12}$ alkyl adamantane which is isomer of 1,3-dimethyl adamantane; calculated from the peak of said compound in gas chromatography excluding the peaks of the other intermediates.
[2] DMA is 1,3-dimethyl adamantane.

1. Preparation of the catalyst

To La-Y(H)-type zeolite (SK-500, Union Carbide Co. Ltd.) platinum, Rhenium and Nickel were held in amounts of 0.75%, 0.25% and 3%, respectively by the method of immersing.

After drying, the catalyst was calcined under air at a temperature of 400° C for 3 hours.

2. Reaction

Into a reaction vessel, predetermined amount of the catalyst was fed and then reduced at a temperature of 400° C for 2 hours in the stream of hydrogen gas (flow rate: 400 cubic centimeter per minute.

After cooling to a predetermined reaction temperature, tetracyclo-(6.2.1.1$^{3,6}$.0$^{2,7}$) dodecane was fed at a predetermined rate. Pressure controlling valve was set to a predetermined pressure when the catalyst layer was wetted evenly with the starting solution. Thereafter, the reaction was started by changing the stream of hydrogen gas to the stream of mixture gas consisting of hydrogen and hydrogen chloride (concentration of hydrogen chloride is set 5.36% or 2.2%) and controlling the flow rate in-order to maintain a molar ratio of tetracyclo-(6.2.1.1$^{3,6}$.0$^{2,7}$) dodecane to the mixture gas to 4:1. The reaction was carried out for more than 16 hours. The reaction solution was analysed by gas chromatography using p-cymene as the internal standard.

What is claimed is:

1. A process for producing alkyl adamantanes which comprises reacting tetracyclo-(6.2.1.1$^{3,6}$.0$^{2,7}$) dodecanes and hydrogen in the presence of H-Y type zeolite or zeolite subjected to ion-exchange with at least one kind of metal ion selected from the group consisting of alkaline earth metals and rare earth metals as a catalyst.

2. A process according to claim 1, wherein the catalyst is a catalyst which is further contained at least one kind of transitional metals.

3. A process according to claim 1, wherein alkaline earth metals are magnesium and calcium.

4. A process according to claim 1, wherein rare earth metals are lanthanum, cerium, niobium, ytterbium and yttrium.

5. A process according to claim 2, wherein transitional metals are iron, cobalt, nickel, platinum, rhenium, copper and rhodium.

6. A process according to claim 2, wherein the catalyst is further contained germanium.

7. A process according to claim 1, wherein the reaction is carried out under the stream of hydrogen gas.

8. A process according to claim 1, wherein the reaction is carried out under the stream of mixture gas consisting of hydrogen and hydrogen chloride.

* * * * *